United States Patent [19]
Negishi et al.

[11] Patent Number: 6,002,037
[45] Date of Patent: Dec. 14, 1999

[54] CHIRAL ORGANOALANES AND THEIR ORGANIC DERIVATIVES VIA ZIRCONIUM-CATALYZED ASYMMETRIC CARBOALUMINATION OF TERMINAL ALKENES

[75] Inventors: Ei-ichi Negishi, West Lafayette, Ind.; Denis Y. Kondakov, Rochester, N.Y.

[73] Assignee: Purdue Research Foundation, West Lafayette, Ind.

[21] Appl. No.: 08/949,831

[22] Filed: Oct. 14, 1997

Related U.S. Application Data

[60] Provisional application No. 60/027,712, Oct. 15, 1996.
[51] Int. Cl.$^6$ .............................. C07F 5/06; C07C 27/00
[52] U.S. Cl. ......................... 556/170; 556/190; 568/815; 568/897; 568/911
[58] Field of Search .................................... 556/170, 190; 568/897, 911, 815

[56] References Cited

PUBLICATIONS

Giacomelli et al., J. Org. Chem., vol. 49, pp. 1725–1728, 1984.
Kondakov, Denis Y., and Negishi, Ei–ichi, "Zirconium–Catalyzed Enantioselective Alkylalumination of Monosubstituted Alkenes Proceeding via Noncyclic Mechanism," The Journal of the American Chemical Society, vol. 118, No. 6, 1996, pp. 1577–1578.
Kondakov, Denis Y., and Negishi, Ei–ichi, "Zirconium–Catalyzed Enantioselective Methylalumination of Monosubstituted Alkenes," *The Journal of the American Chemical Society*, vol. 117, No. 43, 1995, pp. 10771–10772.

*Primary Examiner*—Porfirio Nazario-Gonzalez
*Attorney, Agent, or Firm*—Woodard, Emhardt, Naughton, Moriarty & McNett

[57] ABSTRACT

The present invention describes the Zr-catalyzed asymmetric carboalumination of alkenes to produce chiral alkylalanes that can be converted to various chiral organic compounds, such as isoalkyl alcohols, in highly enantiomeric excess. More particularly, the asymmetric addition of alkylaluminums to terminal alkenes under the influence of a catalyst such as a chiral zirconocene derivative produces chiral alkylaluminums that can be oxidized to 2-alkyl-substituted products (particularly alcohols) in greater than 60% enantiomeric excess. The ee figures can often exceed 95%. The organoalanes produces by the inventive process can be converted to a wide variety of other organic compounds of interest in the production of vitamins, pharmaceuticals and other medicinally and biologically important compounds, including vitamins and antibiotics.

19 Claims, No Drawings

CHIRAL ORGANOALANES AND THEIR ORGANIC DERIVATIVES VIA ZIRCONIUM-CATALYZED ASYMMETRIC CARBOALUMINATION OF TERMINAL ALKENES

This application claims benefit of Provisional Application Ser. No. 60/027,712 filed Oct. 15, 1996.

FIELD OF THE INVENTION

The present invention relates to the Zr-catalyzed asymmetric carboalumination of alkenes to produce chiral alkylalanes that can be converted to various chiral organic compounds, such as isoalkyl alcohols, in highly enantiomeric excess.

BACKGROUND OF THE INVENTION

Catalytic enantioselective carbon-carbon bond formation involving simple alkenes without heteroatom function groups represents a highly desirable but formidable synthetic task. Aside from the long-known asymmetric cyclopropanation catalyzed by various late transition metal complexes, the currently known reactions of this class, including asymmetric carbonyl ene reaction, asymmetric hydroformylation, and asymmetric hydrocyanation, have been reported only within the last several years. It should also be noted that the scope of the carbonyl ene reaction is essentially limited to 1,1-dialkylsubstituted alkenes, and that of the latter two appears to be limited to vinylarenes.

SUMMARY OF THE INVENTION

The present invention describes the Zr-catalyzed asymmetric carboalumination of alkenes to produce chiral alkylalanes that can be converted to various chiral organic compounds, such as isoalkyl alcohols, in highly enantiomeric excess. More particularly, the asymmetric addition of alkylaluminums to terminal alkenes under the influence of a catalyst such as a chiral zirconocene derivative produces chiral alkylaluminums that can be oxidized to 2-alkyl-substituted products (particularly alcohols) in greater than 60% enantiomeric excess. The ee figures can often exceed 95%.

The organoalanes produces by the inventive process can be converted to a wide variety of other organic compounds of interest in the production of vitamins, pharmaceuticals and other medicinally and biologically important compounds, including vitamins and antibiotics.

In one aspect of the invention alkylalanes are prepared by the enantioselective alkylalumination of an alkene substrate. The preferred method comprises reacting an alkene substrate with a reagent combination comprising (a) an alkylaluminum compound, and (b) a catalytic amount of a zirconocene derivative; with the reacting taking place in a halogenated solvent;

In another aspect of the invention organoalanes are prepared by the enantioselective alkylalumination of an alkene substrate. The preferred method comprises:

(a) reacting an alkene substrate with an alkylaluminum compound and a catalytic amount of a zirconocene derivative, with the reacting taking place in a halogenated solvent;

(b) quenching the reaction of step (a) with $O_2$ or HCl or some other suitable electrophile;

(c) treating the product of step (b) with NaOH or other suitable reagent effective to replace the alkylaluminum Al with H; and (d) extracting the desired chiral alkylalane product from the products of step (c).

DESCRIPTION OF THE PREFERRED EMBODIMENT

One aspect of the present invention relates to the reaction of various monosubstituted alkenes containing hydrocarbon substituents with $Me_3Al$ and a catalytic amount of a chiral zirconocene derivative to produce chirally enriched or discriminated alkylalanes. The reaction further provides, after oxidation with $O_2$, 2-methyl-1-alkanols in generally high yeilds with up to 85% ee (typically 70–75% ee) (eq. 1).

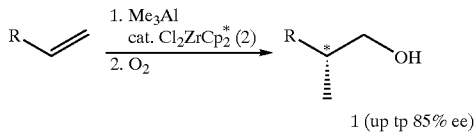

1 (up tp 85% ee)

By way of a representative example, 1-octene may be treated with 1 molar equiv of $Me_3Al$ in 1,2-dichloroethane and dichlorobis(1-neomenthylindenyl)-zirconium 2 (8 mol %) at 22° C. for 12 h under 1 atm of Ar.

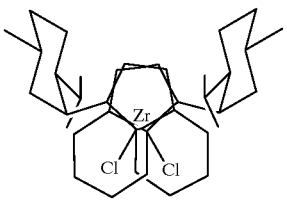

2

Oxygen is then bubbled through the reaction mixture (30 min, 0° C.), and the resultant mixture is further stirred for 6 h under oxygen. After treatment with 15% aqueous NaOH, the usual extractive workup and Kugelrohr distillation provides (2R)-2-methyl-1-octanol (88% yield) in 72% ee as determined from the $^1H$ and $^{13}C$ NMR spectra of the ester derived from (+)- and (−)-MTPA, i.e., α-methoxy-α-(trifluoromethyl)-phenylacetic acid, using the standard procedure.

Representative experimental results obtained with 2 used as a catalyst are summarized in Table 1.

TABLE 1

Zirconium-Catalyzed Methylalumination of Monosubstituted Alkenes[a]

| substrate | time, h | product | yield,[b] % | ee, % |
|---|---|---|---|---|
| (1-octene) | 12 | (2-methyl-1-octanol) | 88 | 72 |

TABLE 1-continued

Zirconium-Catalyzed Methylalumination of Monosubstituted Alkenes[a]

| substrate | time, h | product | yield,[b] % | ee, % |
|---|---|---|---|---|
| 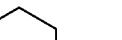 | 12 | 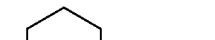 | 92 | 74 |
|  | 12 |  | 80 | 65 |
|  | 24 |  | 77 | 70 |
| 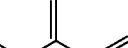 | 528 | 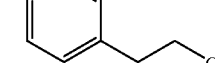 | 30 | 85 |
|  | 12 |  | 81 | 74 |
|  | 12[c] |  | 79 | 75 |
|  | 96[d] | 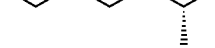 | 68 | 71 |

[a]The reactions were run using 8 mol % of 2 and 1 equiv of Me$_3$Al in 1,2-dichloroethane at 22° C.
[b]Isolated yields.
[c]Three-fold excess of Me$_3$Al was used.
[d]Two-fold excess of Me$_3$Al was used.

As background to the invention, the inventors earlier reported the Zr-catalyzed methylalumination of alkynes, which was shown to proceed via direct addition of the Me—Al bond assisted by a Zr catalyst. It was then found that the corresponding reaction of monosubstituted alkenes with Me$_3$Al—Cl$_2$ZrCp$_2$ did not give the expected methylaluminated products in detectable yields. It should be noted along this line that i-Bu$_3$Al—Cl$_2$—ZrCp$_2$ is a convenient reagent system for hydroalumination, rather than carboalumination, of monosubstituted alkenes, for which the mechanism shown in Scheme 1 appears to be plausible. Although not definitively established, a six-centered transition state represented by 3 may be proposed.

Reinvestigation of the reaction of 1-octene with Me$_3$Al (1 molar equiv) and Cl$_2$ZrCp$_2$ (8 mol %) has now revealed that the products obtained after protonolysis consist of 2-(n-hexyl)-1-decene 4, which accounts for 59% of 1-octene and 2-methyl-1-octene (18%), the yield of the desired 2-methyloctane being <2%. Evidently, the initially formed 2-methyloctylmetal 5 containing Al and/or Zr readily reacts with 1-octene to induce hydrometalation similar to that shown in Scheme 1, to give 2-methyl-1-octene and an n-octylmetal derivative. The latter undergoes carbometalation with 1-octene to give a 2-(n-hexyl)-1-decylmetal derivative, which then undergoes hydrometalation with 1-octene to complete a catalytic cycle producing 4 (Scheme 2).

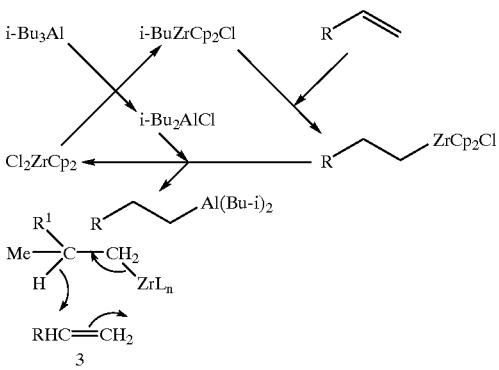

Scheme 1

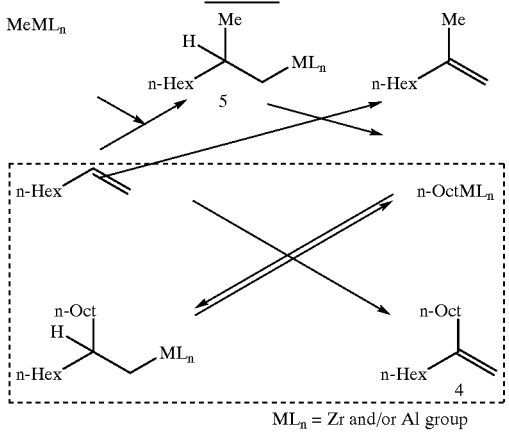

Scheme 2

ML$_n$ = Zr and/or Al group

On the basis of the above mechanistic interpretation, it is now believed that the hydride transfer process between the initially formed methylmetalated product 5 and the starting 1-alkene must be blocked in order to obtain 5 in high yield. For yet unclear reasons, the bulky chiral ligands, e.g., 2, appear to be effective for this purpose. By virtue of their large steric requirements, they effectively block the six-centered interaction depicted in 3.

The observed high ee figures are difficult to explain in terms of direct addition of the Me—Al bond assisted by zirconocene derivatives observed in the Zr-catalyzed methyl-alumination of alkynes. On the other hand, the results appear to be more consistent with direct Me—Zr bond addition promoted by organaluminum species, in line with the widely believed mechanism for the homogeneous Ziegler-Natta-type reactions.

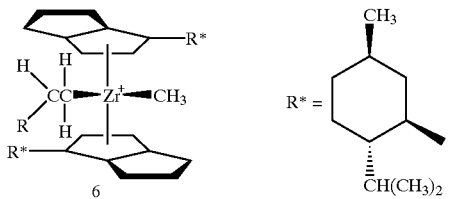

In the light of the X-ray structure of 2, the uniformly observed R configuration of 2-methyl-1-alkanols 1 in cases where 2 was the catalyst not only is consistent with the four-centered syn Me—Zr addition, as depicted in 6, but also lends further support for the direct Me—Zr bond addition mechanisms. The X-ray structure of 2 indicates that the four octants on the back side are not available for chemical transformations. In the transition state model 6, both Zr—CH$_3$ σ orbital and empty orbitals are on the front side. The upper right and lower left octants are more open than the other two and hence accommodate the R group of a mono-substituted alkene, leading to Zr-alkene interaction on the Re face of the alkene and subsequent formation of a (2R)-2-methyl-1-alkanol.

Yet another aspect of the reaction shown in eq. 1 is that methylalanes can undergo Zr-catalyzed methylalumination with alkenes, which is totally discrete from the known reaction of ethylalanes producing 3-alkylaluminacyclopentanes via cyclic carbozirconation. In fact, the reaction of 1-octene with Et$_3$Al (1 molar equiv) and 2 (8 mol %) in hexanes gave, after oxidation, a 69% yield of 2-(n-hexyl)-1,4-butanediol in only 36% ee.

As indicated in Table 1, the methylalumination of mono-substituted alkenes with Me$_3$Al and a catalytic amount of 2 is reasonably general with respect to the substituent in the starting alkenes. Thus, those containing n-Hex, i-Bu, cyclohexyl, and benzyl are converted to the corresponding (2R)-2-methyl-1-alkanols of 65–92% yields. Styrene is converted to (2R)-2-phenyl-1-propanol of 85% ee, albeit in low yield (30%).

Particularly encouraging are the results observed with heteroatom-containing 1-alkenes. Both 5-hexen-1-ol and 4-pentenyldiethylamine proceeded normally and satisfactorily to give the corresponding 2-methyl-1-alkanols of 75 and 71% ee, respectively, while diallyldimethylsilane provided (3,3,5-trimethyl-3-silacyclohexyl)methanol, which was >95% cis and 74% ee, in 81% yield.

It is to be appreciated that other chiral catalysts may be used in the inventive process, although other chiral catalysts tested thus far have been less satisfactory. Specifically, the reaction of 1-octene with Me$_3$Al (1 molar equiv) in the presence of 8 mol % of bis-(1-neoisomenthylindenyl) zirconium dichloride, bis(1-neoisomentyl-4,5,6,7-tetrahydroindenyl)-zirconium dichloride, (R,R)-ethylenebis (4,5,6,7-tetrahydro-1-indenyl)-zirconium dichloride, and (R,R)-ethylenebis(4,5,6,7-tetrahydro-1-indenyl)-zirconium (R)-1',1''-bi-2-naphtholate gave 2-methyl-1-octanol of 50% ee (S, 67%), 6% ee (S, 60%), 8% ee (R, 45%), and 6% ee (R, 53%), respectively, in the yields shown in parentheses.

In view of a large number of natural products that are either represented by or accessible via 2-methyl-1-alkanols, the potential synthetic significance of this reaction is evident.

Another aspect of the present invention relates to the more general alkylalumination of alkene substrates to produce chiral alkylalanes. Although early development of the enantioselective methylalumination of monosubstituted alkenes had been successful, the initial outlook for achieving a similar Zr-catalyzed enantioselective alkylmetalation with ethyl-, propyl-, and higher alkylmetals was not promising.

As background, the reaction of monosubstituted alkenes with EtMgX, where X is Cl or Br, in the presence of a catalytic amount of Cp$_2$ZrCl$_2$ was known to give (2-ethylalkyl)magnesium halides. The reaction had been shown to proceed via a cyclic mechanism, and its successful application to the development of a cyclic enantioselective carbometalation--elimination tandem reaction involving cyclic, allylic ethers and amines had been reported. However, attempts to develop Zr-catalyzed enantioselective conversion of monosubstituted alkenes into (2-ethylalkyl) magnesium halides had led only to very disappointing results.

Also known was the reaction of monosubstituted alkenes with Et$_3$Al, catalyzed by Cp$_2$ZrCl$_2$, producing aluminacyclopentanes, e.g., 1 but the reaction of 1-decene with 1 equiv of Et$_3$Al in the presence of 8 mol % of dichlorobis(neomenthylindenyl)zirconium 2 in hexanes produced, after oxidation, a 65% yield of 2-(n-octyl)-1,4-butanediol 8 in only 33% ee (Scheme 3).

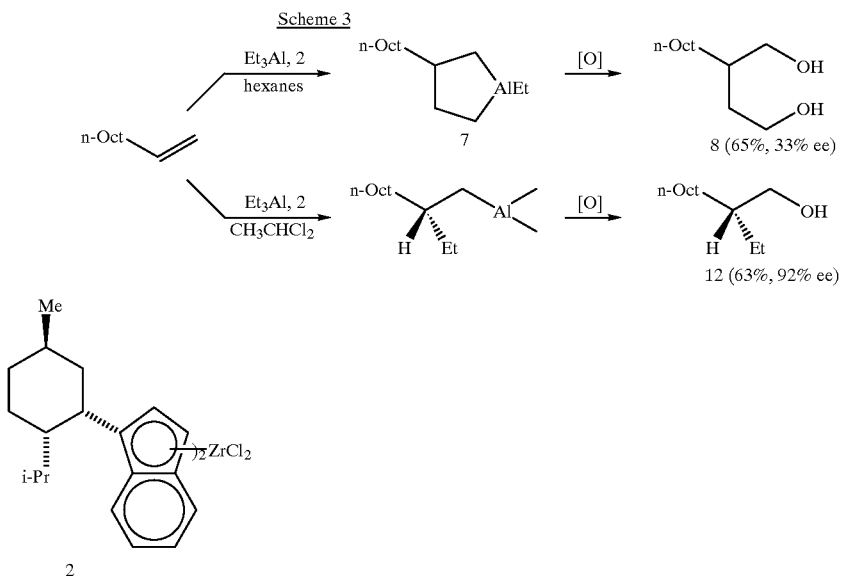

Interestingly, the reaction of 1-decene with 1 equiv of Et$_3$Al in the presence of 8 mol % of Cp$_2$ZrCl$_2$ in (CH$_2$Cl)$_2$ in place of hexanes produced, after deuterolysis, a 37% yield of 3-(deuteriomethyl)undecane 9, which contained D in the C-1 position only to the extend of 9% The extent of D incorporation the deuteriomethyl group was >90%. 2-Ethyl-1-decene 10 and 1-deuteriodecane 11 were also obtained in 20% yield each (eq. 2).

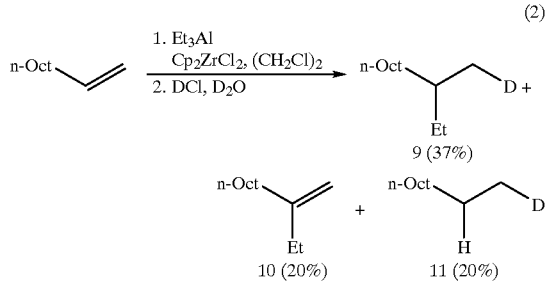

Accordingly, it has been determined that, in polar solvents, e.g., (CH$_2$Cl), noncyclic ethylalumination similar to methylalumination, partially accompanied by competitive hydroalumination involving a (2-ethyldecyl)alane, can take place in preference to the previously reported cyclic carbometalation processes.

In one aspect of the present invention therefore, 1-decene is treated with Et$_3$Al in (CH$_2$Cl)$_2$ at 25° C. using 8 mol % of 2 as a catalyst. After oxidation with O$_2$, a 65% yield of (R)-2-ethyl-1-decanol 12 in 68% ee is obtained.

In view of the dramatic solvent effects discussed above, various halogenated solvents have been screened, and it has been determined that the use of CH$_3$CHCl$_2$ or CH$_2$CL$_2$ in place of (CH$_2$Cl)$_2$ boosts the % ee figures to the 80s. They are further increased to the 90–95% range for various monosubstituted alkenes by lowering the reaction temperature to 0° C. Some representative results are summarized in Table 2.

TABLE 2

| | | Zirconium-Catalyzed Alkylalumination of Monosubstituted Alkenes[a] | | | | | | |
|---|---|---|---|---|---|---|---|---|
| substrate | R of R$_3$Al | solvent | temp ° C. | time h | quenching agent | product | yield[b] % | % ee |
| n-Bu-CH=CH$_2$ | Et | (CH$_2$Cl)$_2$ | 25 | 4 | O$_2$ | n-Bu-CH(Et)-CH$_2$OH | 65 | 68 |
| n-Bu-CH=CH$_2$ | Et | C$_6$H$_5$Cl | 25 | 4 | O$_2$ | n-Bu-CH(Et)-CH$_2$OH | 70 | 68 |

TABLE 2-continued

Zirconium-Catalyzed Alkylalumination of Monosubstituted Alkenes[a]

| substrate | R of R$_3$Al | solvent | temp °C. | time h | quenching agent | product | yield[b] % | % ee |
|---|---|---|---|---|---|---|---|---|
| n-Bu–CH=CH$_2$ | Et | 1,2-Cl$_2$C$_6$H$_4$ | 25 | 4 | O$_2$ | n-Bu-CH(Et)-CH$_2$OH | 72 | 67 |
| n-Bu–CH=CH$_2$ | Et | CH$_2$Cl$_2$ | 25 | 6 | O$_2$ | n-Bu-CH(Et)-CH$_2$OH | 57 | 81 |
| n-Bu–CH=CH$_2$ | Et | CH$_2$Cl$_2$ | 0 | 6 | O$_2$ | n-Bu-CH(Et)-CH$_2$OH | 63 | 92 |
| n-Bu–CH=CH$_2$ | Et | CH$_2$Cl$_2$ | −25 | 6 | O$_2$ | n-Bu-CH(Et)-CH$_2$OH | 60 | 94 |
| n-Bu–CH=CH$_2$ | Et | CH$_3$CHCl$_2$ | 25 | 6 | O$_2$ | n-Bu-CH(Et)-CH$_2$OH | 70 | 86 |
| n-Bu–CH=CH$_2$ | Et | CH$_3$CHCl$_2$ | 0 | 24 | O$_2$ | n-Bu-CH(Et)-CH$_2$OH | 74 | 93 |
| n-Oct–CH=CH$_2$ | Et | CH$_3$CHCl$_2$ | 0 | 12 | O$_2$ | n-Oct-CH(Et)-CH$_2$OH | 64 | 92 |
| i-Bu–CH=CH$_2$ | Et | CH$_3$CHCl$_2$ | 0 | 24 | O$_2$ | i-Bu-CH(Et)-CH$_2$OH | 77 | 90 |
| Ph-CH$_2$-CH=CH$_2$ | Et | CH$_3$CHCl$_2$ | 0 | 24 | O$_2$ | Ph-CH$_2$-CH(Et)-CH$_2$OH | 69 | 93 |
| HO(CH$_2$)$_4$–CH=CH$_2$ | Et[c] | CH$_3$CHCl$_2$ | 10 | 24 | HCl | HO(CH$_2$)$_4$-CH(Et)-CH$_3$ | 88 | 90 |
| Et$_2$N(CH$_2$)$_3$–CH=CH$_2$ | Et[d] | CH$_3$CHCl$_2$ | 25 | 72 | O$_2$ | Et$_2$N(CH$_2$)$_3$-CH(Et)-CH$_2$OH | 56 | 95 |

TABLE 2-continued

Zirconium-Catalyzed Alkylalumination of Monosubstituted Alkenes[a]

| substrate | R of $R_3Al$ | solvent | temp °C. | time h | quenching agent | product | yield[b] % | % ee |
|---|---|---|---|---|---|---|---|---|
| Me-Si(Me)(allyl)(allyl) (diallyldimethylsilane) | Et | $CH_3CHCl_2$ | 0 | 24 | $O_2$ | cyclohexane with $Me_2Si$, Et, $CH_2OH$ | 66 | 96 |
| $HO(CH_2)_4$-CH=CH$_2$ | n-Pr[c] | $CH_3CHCl_2$ | 10 | 24 | HCl | $HO(CH_2)_4$-CH(n-Pr)-CH$_3$ | 90 | 91 |
| n-Oct-CH=CH$_2$ | n-Pr | $CH_3CHCl_2$ | 0 | 12 | $O_2$ | n-Oct-CH(n-Pr)-CH$_2$OH | 62 | 91 |
| n-Pr-CH=CH$_2$ | n-Oct | $CH_3CHCl_2$ | 0 | 12 | $O_2$ | n-Oct-CH(n-Pr)-CH$_2$OH | 59 | 85 |

[a]The reactions were run using 8 mol % of 2 and 1 equiv of $R_3Al$, unless otherwise stated.
[b]Isolated yields.
[c]Three-fold excess of $R_3Al$ was used.
[d]Two-fold excess of $R_3Al$ was used.

The % ee figures were determined from the $^1H$ NMR spectra of the (+)- and (−)-MTPA esters. In most cases, the $CH_2$ group directly bonded to OH showed distinct signals for the two diasteromers. In the cases of (r)-2-ethyl-1-hexanol and (r)-2-ethyl-1-decanol, the $CH_3$ signals for the ethyl substituent were used for this purpose. As in the methylalumination with $Me_3$—Al and 2, alkylmetalation takes place selectively and uniformly on the re face of alkenes.

The optimized % ee figures range from 90 to 95% except for one case involving (n-Oct)$_3$Al, where the product was 85% ee. Here again, the presence of remote hydroxy and amino groups may not significantly affect the course of reaction, and diallyldimethylsilane underwent an inter-intra tandem carbometalation exhibiting >92% de and 96% ee stereoselectivity figures. On the other hand, ethylalumination of styrene gave an intractable product, and that of cyclohexylethene did not proceed over 12 h at 25° C.

The highly favorable results observed in ethylalumination in $CH_3CHCl_2$ may also be applied to the methylalumination reaction described above. Under otherwise the same conditions, the reaction of 1-octene with $Me_3Al$ in the presence of 8 mol % of 2 at 25° C. in $CH_3CHCl_2$ gave, after oxidation, an 83% yield of (R)-2-methyl-1-octanol in 81% ee, corresponding to an increase by roughly 10% in % ee. Evidently, % ee figures for ethylalumination are 10–15% higher than the corresponding figures for methylalumination under comparable conditions. On the other hand, the yields of ethylalumination are slightly but unmistakably lower than those of methylalumination.

A detailed analysis of the products of the above reaction indicate the presence of 3-methylundecane (17%), decane (2%), and the unreacted 1-decene (2%). No more than traces, if any, of 2-ethyl-1-decene and dimeric products are present. Clearly, the lower yield is not due to competitive hydrometalation. Since the results of deuterolysis with DCl-$D_2O$ closely parallel those of oxidation, the origin of 3-methylundecane does not appear to be due to incomplete oxidation. It must have been formed during the carboalumination itself. The use of $(CH_2Cl)_2$ and $CH_2Cl_2$ led to its formation in 12 and 11%, respectively. The fact that the reaction run in $CD_2Cl_2$ followed by protonolysis with 3 NHCl does not incorporate D suggests that the solvents are not likely to be the sources of hydrogen. One likely process that might be responsible for the formation of 3-methylundecane is M-H exchange via σ-bond methathesis, although this point needs to be further clarified.

It is also to be appreciated that the scope of this reaction is not restricted to ethylalumination. Thus, the reaction of 5-hexen-1-ol with 3 equiv of (n-Pr)$_3$Al in $CH_3CHCl_2$ in the presence of 8 mol % of 2 at 10° C. for 24 h provided, after protonolysis, a 90% yield of (R)-5-methyl-1-octanol in 91% ee.

It is worth noting that the n-Pr group of (n-Pr)$_3$Al is incorporated as such. Any cyclic processes involving alkene-zirconocene derivatives would incorporate the same group as an i-Pr group. Both R and S isomers of 2-(n-propyl)-1-decanol can be prepared by n-propylalumination of 1-decene and n-octylalumination of 1-pentene, respectively, using the same catalyst 2 (Scheme 4).

Scheme 4

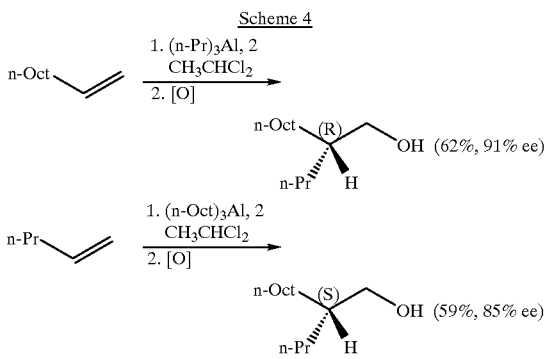

In a further aspect of the invention, chirally enriched or discriminated alkylalanes of the formula

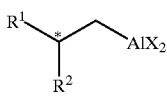
(I)

are produced by treating terminal alkenes with a reagent system comprising one or more alanes and a chiral catalyst. In the above formula:

$R^1$ is a member selected from the group consisting of optionally substituted alkyls and heteroalkyls;

$R^2$ is a member selected from the group consisting of optionally substituted alkyls and heteroalkyls; wherein $R^2$ is capable of participating in Zr-catalyzed carboalumination; and each X is independently a member selected from the group consisting of optionally substituted alkyls and heteroalkyls.

As can be seen from the foregoing discussion, $R^1$ can be any of a wide variety of substituents, since the $R^1$ group does not take an active role in the reaction described above. Accordingly, no particular limitation of the length of $R^1$, or on the heteroatoms that may be included therein, is required so long as $R^1$ does not interfere with the carboalumination taking place at the terminal olefin bond. Straight chain alkyls, branched chain alkyls and aromatics, all with or without heteroatoms or other substituents, may be used at $R^1$.

$R^2$ has somewhat greater limitation, since $R^2$ is involved in the carboalumination. Accordingly, straight chain alkyls are preferred at $R^2$, although other groups that do not interfere with the Zr-catalyzed carboalumination may be used. Specific examples provided above include Me, Et, n-Pr and n-Oct.

Each $X_i$ is limited similarly to $R^2$, since those groups also are "involved" in the Zr-catalyzed carboalumination. Each $X_i$ may be the same, and may be the same as $R^1$, or all three substituents may be different.

As indicated above, the reagent system comprises an alane and a chiral catalyst. The reagent alane is preferably an alkylalane, and most preferably a trialkylalane of the formula:

$R_3Al$ where each R is independently a member selected from the group consisting of Me, Et and other alkyls such as n-Pr and n-Oct. In some preferred embodiments each of $R_{1-3}$ is a straight-chain alkyl, while in some preferred embodiments each $R_{1-3}$ is a branched-chain alkyl. In all cases, the alane selectively breaks the terminal alkene bond under the described catalytic conditions, to provide a chirally enriched alkylalane as shown in scheme 2 above.

The chiral catalyst is preferably a chiral zirconium catalyst of the formula:

$Cp^*{}_2ZrL_n$ where

Cp* is a cyclopentadienyl derivative including indenyl and partially hydrogenated indenyl;

$L_n$ is a ligand such as $Cl_2$, $Br_2$, $I_2$, etc. Other chiral catalysts which bind the alkylalane to the terminal carbon of the alkene with high facial specificity may also be used.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates. In particular, reference will now be made to specific examples using the processes described above. It is to be understood that the examples are provided to more completely describe preferred embodiments, and that no limitation to the scope of the invention is intended thereby.

EXAMPLE 1

(2R)-2-Methyl-1-octanol. In a dry, round-bottomed flask equipped with a stirring bar and a mercury bubbler were placed 1,1-dichloroethane (3 mL), bis(1-neomenthylindenyl)zirconium dichloride (0.053 g, 0.08 mmol), and $Me_3Al$ (0.072 g, 0.96 mL, 1 mmol). To this mixture was added 1-octene (0.112 g, 0.156 mL, 1 mmol) under an argon atmosphere. After stirring the reaction mixture at 22° C. for 12 h, it was cooled to 0° C., whereupon dry oxygen was bubbled through for 30 min. The resultant mixture was further stirred under oxygen atmosphere for 6 h, then treated with 15% aqueous NaOH, extracted with $Et_2O$, washed with brine, dried over anhydrous $MgSO_4$, filtered, and concentrated. Column chrimatography on silica gel (hexane/ether=5/1) provided 0.120 g (83%) of the title compound. Enantiomeric excess was determined from $^1H$ spectra of the esters formed from (+)- and (−)-MTPA using standard procedure: 81% ee, $[\alpha]^{20}D+8.50$ (c 2.3, $CH_2Cl_2$), $^1H$ NMR ($CDCl_3$. $Me_4Si$) δ 0.8–1.0 (m, 6H), 1.05–1.8 (m, 11 H)), 2.30 (s, 1 H), 3.3–3.6 (m,2H); $^{13}C$ NMR ($CDCl_3$, $Me_4Si$) δ 14.12, 16.77, 22.69, 27.03, 29.67, 31.90, 30.33, 35.94, 67.94. MS [M-H]$^+$ 143.

EXAMPLE 2

(2R)-2-Ethyl-1-hexanol. In a dry, round-bottomed flash equipped with a stirring bar and a mercury bubbler were placed 1,1-dichloroethane (3 mL), bis(1-neomenthylindenyl)-zirconium dichloride (0.053 mg, 0.08 mmol), and $Et_3Al$ (0.114 g, 0.14 ML, 1 mmol). To this mixture was added 1-hexene (0.084 g, 0.125 mL, 1 mmol) under an argon atmosphere. After stirring the reaction mixture at 0° C. for 12 h, oxygen was bubbled through for 30 min. The resultant mixture was further stirred under oxygen atmosphere at 22° C. for 6 h, then treated with 15% aqueous NaOH, extracted with Et$_2$O, washed with brine, dried over anhydrous MgSO$_4$, filtered, and concentrated. Column chromatography on silica gel (hexane/ether=4/1) provided 0.096 g (74%) of the title compound. Enantiomeric excess was determined from H NMR spectra of the (+)- and (−)-MTPA esters using standard procedure: 93% ee, [α]$^{20}$D$^{-2.9°}$ (C 1.5, CH$_2$Cl$_2$), $^1$H M,R (CDCl$_3$, Me$_4$Si) δ 0.8–1.0 (m, 6 H), 1.1–1.6 (m, 10 H), 3.4–3.6 (m, 2H); $^{13}$C NMR (CDCl$_3$, Me$_4$Si) δ 11.19, 14.18, 23.19, 23.45, 29.22, 30.23, 42.08, 65.41. MS [M-H]$^+$ 129. IR (neat) 3346, 1460, 1118 cm$^{-1}$.

EXAMPLE 3

(5R)-5-Methyl-1-heptanol. In a dry, round-bottomed flask equipped with a stirring bar and a mercury bubbler were placed 1,1-dichloroethane (3 mL), bis(1-neomenthylindenyl)zirconium dichloride (0.053 mg, 0.08 mmol), and Et$_3$Al (0.343 g, 0.41 mL, 3 mmol). To this mixture was added 5-hexene-lol (0.100 g, 0.12 mL, 1 mmol) under an argon atmosphere at 0° C. After stirring the reaction mixture at 10° C. for 24 h, the resultant mixture was cooled to −20° C., treated with 15% aqueous NaOH, extracted with Et$_2$O, washed with brine, dried over anhydrous MgSO$_4$, filtered, and concentrated. Column chromatography on silica gel (hexane/ether=4/1) provided 0.114 g (88%) of the title compound. Enantiomeric excess was determined from $^1$H NMR spectra of the (+)- and (−)-MTPA esters using standard procedure: 90% ee, [α]$^{20}$D −8.9° (c 5.6, CH$_2$Cl$_2$), $^1$H NMR (CDL$_3$, Me$_4$Si) δ 0.8–0.9 (m, 6 h), 1.0–1.6 (m, 9 H), 1.88 (s, 1 H), 3.63 (t, J=6.6 Hz, 2 H); $^{13}$C dNMR (CDCl$_3$, Me$_4$Si) δ 11.40, 19.16, 23.28, 29.45, 33.14, 34.40, 36.41, 63.01. MS [M-H]$^+$ 129. IR (neat) 3334, 1462, 1378, 1056 cm$^{-1}$.

EXAMPLE 4

(2R)-2-Propyl-1-decanol. In a dry, round-bottom flask equipped with a stirring bar and a mercury bubbler were placed 1,1-dichloroethane (3 mL), bis(1-neomenthylindenyl)zirconium dichloride (0.053 mg, 0.08 mmol), and n-Pr$_3$Al (0.156 g, 0.19 mL, 1 mmol). To this mixture was added 1-decene (0.140 g, 0.19 mL, 1 mmol) under an argon atmosphere. After stirring the reaction mixture at 0° C. for 12 h, oxygen was bubbled through for 30 min. The resultant mixture was further stirred under oxygen atmosphere at 22° C. for 6 h, then treated with 15% aqueous NaOH, extracted with Et$_x$O, washed with brine, dried over anhydrous MgSO$_4$, filtered, and concentrated. Column chromatography on silica gel (hexane/ether=4/1) provided 0.124 mg (62%) of the title compound. Enantiomeric excess was determined from $^1$H NMR spectra of the (+)- and (−)-MTPA esters using standard procedure: 90% ee, [α]$^{20}$D −0.8° (c 2.2, CH$_2$Cl$_2$), $^1$H NMR (CDCl$_3$, Me$_4$Si) δ 0.85–0.95 (m, 6 h), 1.15–1.55 (m, 19 H0, 1.62 (s, 1 h), 3.52 (d, J=5.5 Hz, 2 H); $^{13}$C NMR (CDCl$_3$, Me$_4$Si) δ 14.13, 14.50, 20.05, 22.72, 26.94, 29.39, 29.62, 30.14, 30.98, 31.95, 33.30, 40.34, 65.70. MS [M-H]$^+$ 199. IR (neat) 3332, 1466, 1378, 1040 cm$^{-1}$.

EXAMPLE 5

(2S)-2-Propyl-1-decanol. In a dry, round-bottomed flask equipped with a stirring bar and a mercury bubbler were placed 1,1-dichloroethane (3 mL), bis(1-neomenthylindenyl)zirconium dichloride (0.053 mg. 0.08 mmol), and n-Oct$_3$Al (0.366 g, 1 mmol). To this mixture was added 1-pentene (0.070 g, 0.110 mL, 1 mmol) under an argon atmosphere. After stirring the reaction mixture was further stirred under oxygen atmosphere at 22° C. for 6 h, then treated with 15% aqueous NaOH, extracted with Et$_2$O, washed with brine, dried over anhydrous MgSO$_4$, filtered, and concentrated. Column chromatography on silica gel (hexane/ether=4/1) provided 0.118 mg (59%) of the title compound. Enantiomeric excess was determined from $^1$H NMR spectra of the (+)- and (−)-MTPA esters using standard procedure: 85% ee, [α]$^{20}$D ++0.6° (c 1.5, CH$_2$Cl$_2$), $^1$H NMR (CDCl$_3$, Me$_4$Si) δ 0.85–0.95 (m, 6 H), 1.15–1.55 (m, 19 H), 1.6 (s, 1 H), 3.53 (m, 2 H); $^{13}$C NMR (CDCl$_3$, Me$_4$Si) δ 14.14, 14.50, 20.05, 22.72, 26.93, 29.39, 29.67, 30.14, 30.96, 31.95, 33.28, 40.33, 65.69. MS [M-H]$^+$ 199. IR (neat) 3332, 1466, 1378, 1040 cm$^{-1}$.

EXAMPLE 6

(2R)-2-Methyl-3-phenyl-1-propanol. In a dry, round-bottomed flask equipped with a stirring bar and a mercury bubbler were placed 1,2-dichloroethane (3 mL), bis(1-neomenthylindenyl) zirconium dichloride (53 mg. 0.08 mmol), and 2M trimethyl aluminum in toluene (0.5 mL, 1 mmol). To this mixture was added allybenzene (0.118 g, 0.113 mL, 1 mmol) under an argon atmosphere. After stirring the reaction mixture at 22° C. for 24 h, it was cooled to 0° C., whereupon oxygen was bubbled though for 30 min. The resultant mixture was further stirred under oxygen atmosphere for 6 h, then treated with 15% aqueous NaOH, extracted with Et$_2$O, washed with brine, dried over anhydrous MgSO$_4$, filtered, and concentrated. Column chromatography on silica gel (hexane/ether=4/1) provided 0.116 gf (77%) of the title compound. Enantiomeric excess was determined from $^1$H and $^{13}$C NMR spectra of the esters formed from (+)- and (−)-MTPA using standard procedure: 70% ee, [α]$^{20}$D +6.9° (c 1.9, CH$_2$Cl$_2$). $^1$H NMR (CDCl$_3$, Me$_4$Si) δ 0.88 (d, J=6.8 Hz, 3 H), 1.8–2.0 (m, 1 H), 2.2–2.45 (m, 2 H), 2.7–2.85 (m, 1 H), 3.35–3.55 (m; 2H), 7.05–7.35 (m, 5 H); $^{13}$C NMR (CDCl$_3$, Me$_4$Si) δ 16.40, 37.72, 39.65, 67.44, 125.79, 128.19, 129.11, 140.64, MS [M]$^1$ 150.

EXAMPLE 7

(2R)-2-,Methyl-3-phenylpropyl(dimethyl)alane. In a dry, round-bottomed flask equipped with a stirring bar and a mercury bubbler were placed dichloromethane-d$_2$ (3 mL), bis(1-neomenthylindenyl) zirconium dichloride (0.053 g, 0.08 mmol), mesitylene (used as an internal standard: 0.050 mL, 0.36 mmol), and Me$_3$Al (0.072 g, 0.96 mL, 1 mmol). To this mixture was added allylbenzene (0.118 g, 0.133 mL, 1 mmol) under an argon atmosphere. After 18 h at 22° C. NMR examination showed that the title compound was formed in 89% yield. Structural assignments were performed using COSY and HETCOR 2D NMR experiments: $^1$H NMR (CD$_2$Cl$_2$, Me$_4$Si) δ −0.35 (s, 6 H, CH$_3$—Al), −0.15–0.15 (m, 2 H, CH$_2$—Al), 0.99 (d, J=6.5 Hz, 3 H, CH$_3$—CH), 1.85–2.00 (m, 1 H, CH), 2.25–2.40 (m, 1 H, CH$_2$-Ph), 2.50–2.65 (m, 1 H, CH$_2$-Ph), 7.10–7.40 (m, 0,5 H, Ph); $^{13}$C NMR (CD$_2$Cl$_2$ Me$_4$Si) δ −7.12 (2 C, CH$_3$—Al), 21.10 (br, 1 C, CH$_2$—Al), 25.89 (1 C, CH$_3$—CH), 34.58 (1 C, CH), 48.25 (1 C, CH$_2$-Ph), 126.77 (1 C, Ph), 128.86 (2 C, Ph), 129.92 (2 C, Ph), 144.11 (1 C, Ph), $^{27}$Al NMR (CD$_2$Cl$_2$, external Al(H$_2$O)6$^{3+}$) δ 160 (W$_{1/2}$=3177 Hz).

While the invention has been illustrated and described in detail in the foregoing description, the same is to be considered as illustrative and not restrictive in character, it being understood that only the preferred embodiments have been shown and described, and that all changes and modifications that come within the spirit of the invention are desired to be protected.

What is claimed is:

1. A chirally enriched mixture of isomers of an alkylalane of the formula:

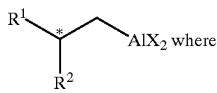 (I)

$R^1$ is a member selected from the group consisting of optionally substituted alkyls and heteroalkyls;

$R^2$ is a member selected from the group consisting of optionally substituted alkyls and heteroalkyls; wherein $R^2$ is not the same as $R^1$; and further wherein $R^2$ is capable of participating in Zr-catalyzed carboalumination; and each X is independently a member selected from the group consisting of optionally substituted alkyls and heteroalkyls;

wherein said chirally enriched mixture comprises an enantiomeric excess of the subject alkylalane.

2. A reagent combination for converting terminal alkene compounds to chirally enriched alkylalanes of the formula:

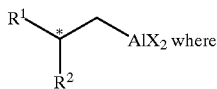 (I)

$R^1$ is a member selected from the group consisting of optionally substituted alkyls;

$R^2$ is a member selected from the group consisting of optionally substituted alkyls, wherein $R^2$ is not the same as $R^1$; and each X is independently a member selected from the group consisting of optionally substituted alkyls;

said reagent combination comprising:
(a) an alane of the formula $R_3Al$; and
(b) a catalyst effective for binding the alane to the substrate alkene with increased facial specificity;

wherein each $R_i$ of said alane is a substituent capable of participating in Zr-catalyzed carboalumination.

3. A method for producing chirally enriched alkylalanes of the formula:

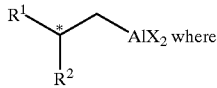 (I)

$R^1$ is a member selected from the group consisting of optionally substituted alkyls;

$R^2$ is a member selected from the group consisting of optionally substituted alkyls; wherein $R^2$ is not the same as $R^1$; and further wherein $R^2$ is capable of participating in Zr-catalyzed carboalumination; and each X is independently a member selected from the group consisting of optionally substituted alkyls;

said method comprising reacting an alkene substrate with an alane of the formula $R_3Al$ and a catalyst effective for binding the alane to the substrate alkene with high facial specificity.

4. The method of claim 3 wherein said catalyst is a zirconocene derivative of the formula:

where
Cp* is a cyclopentadienyl derivative including indenyl and partially hydrogenated indenyl;
$L_n$ is a ligand such as $Cl_2$, $Br_2$, $I_2$, etc.

5. The method of claim 3, wherein said reacting takes place in a halogenated solvent.

6. A method for the enantioselective alkylalumination of an alkene substrate; said method comprising:
(a) reacting an alkene substrate with an alkylaluminum compound and a catalyst effective for binding the alkylaluminum compound to the substrate alkene with high facial specificity; and
(b) converting the chiral alkylalane produced in step (a) to the corresponding optically active organic compound.

7. The method of claim 6 wherein said converting step comprises reacting the alkylalane of step (a) with $O_2$ or HCl or some other suitable electrophile, followed, as needed, by suitable quenching and/or workup.

8. The method of claim 7 and further including the step of extracting the desired chiral alkylalane product from the products of step (b).

9. The method of claim 6 wherein said catalyst is a zirconocene derivative of the formula:

where
Cp* is a cyclopentadienyl derivative including indenyl and partially hydrogenated indenyl;
$L_n$ is a ligand such as $Cl_2$, $Br_2$, $I_2$, etc.

10. The method of claim 6 wherein said reacting takes place in a halogenated solvent.

11. The method of claim 6 wherein said chiral alkylalane product is obtained in an enantiomeric excess of at least 5%.

12. The method of claim 9 wherein said chiral alkylalane product is obtained in an enantiomeric excess of at least 30%.

13. A method of producing a chirally enriched alcohols of the formula:

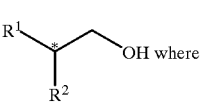 (I)

$R^1$ is a member selected from the group consisting of optionally substituted alkyls; and $R^2$ is a member selected from the group consisting of optionally substituted alkyls; wherein $R^2$ is not the same as $R^1$; and further wherein $R^2$ is capable of participating in Zr-catalyzed carboalumination; said method comprising:
(a) reacting an alkene substrate with an alkylaluminum compound and a catalyst effective for binding the alkylaluminum compound to the substrate alkene with high facial specificity; and
(b) converting the chiral alkylalanes produced in step (a) to the corresponding optically active alcohol.

14. The method of claim 6 wherein said converting step comprises-reacting the alkylalane of step (a) with $O_2$ or HCl or some other suitable electrophile, followed, as needed, by suitable quenching and/or workup.

15. The method of claim 14 and further including the step of extracting the desired chiral alkylalane product from the products of step (b).

16. The method of claim 14 wherein said catalyst is a zirconocene derivative of the formula:

$$Cp^*_2ZrL_n$$

where
- Cp* is a cyclopentadienyl derivative including indenyl and partially hydrogenated indenyl;
- $L_n$ is a ligand such as $Cl_2$, $Br_2$, $I_2$, etc.

17. The method of claim 14 wherein said reacting takes place in a halogenated solvent.

18. The method of claim 11 wherein said chiral alkylalane product is obtained in an enantiomeric excess of at least 5%.

19. The method of claim 11 wherein said chiral alkylalane product is obtained in an enantiomeric excess of at least 30%.

* * * * *